United States Patent
Yonce et al.

(10) Patent No.: US 7,412,287 B2
(45) Date of Patent: Aug. 12, 2008

(54) AUTOMATIC SENSING VECTOR SELECTION FOR MORPHOLOGY-BASED CAPTURE VERIFICATION

(75) Inventors: David J. Yonce, Fridley, MN (US); David Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 465 days.

(21) Appl. No.: 10/744,911

(22) Filed: Dec. 22, 2003

(65) Prior Publication Data

US 2005/0137638 A1  Jun. 23, 2005

(51) Int. Cl.
*A61N 1/37* (2006.01)

(52) U.S. Cl. ........................................ 607/28
(58) Field of Classification Search .................. 607/27, 607/28, 9; 600/510
See application file for complete search history.

(56) References Cited

U.S. PATENT DOCUMENTS

| | | | |
|---|---|---|---|
| 4,832,041 A | 5/1989 | Wang et al. | |
| 4,895,152 A | 1/1990 | Callaghan et al. | |
| 5,273,049 A | 12/1993 | Steinhaus et al. | |
| 5,312,445 A | 5/1994 | Nappholz et al. | |
| 5,330,511 A | 7/1994 | Boute | |
| 5,331,966 A | 7/1994 | Bennett et al. | |
| 5,334,220 A | 8/1994 | Sholder | |
| 5,340,361 A | 8/1994 | Sholder | |
| 5,350,410 A | 9/1994 | Kleks et al. | |
| 5,391,192 A | 2/1995 | Lu et al. | |
| 5,458,623 A | 10/1995 | Lu et al. | |
| 5,534,016 A | 7/1996 | Boute | |
| 5,626,623 A | 5/1997 | Kieval et al. | |
| 5,660,184 A | 8/1997 | Donehoo et al. | |
| 5,674,254 A | 10/1997 | van Krieken | |
| 5,741,308 A | 4/1998 | Sholder | |
| 5,755,739 A | 5/1998 | Sun et al. | |
| 5,771,898 A | 6/1998 | Marinello | |
| 5,778,881 A | 7/1998 | Sun et al. | |
| 5,782,888 A | 7/1998 | Sun et al. | |
| 5,830,150 A | 11/1998 | Palmer et al. | |
| 6,029,088 A | 2/2000 | Budgifvars et al. | |
| 6,101,416 A | 8/2000 | Sloman | |
| 6,128,535 A | 10/2000 | Maarse | |
| 6,169,921 B1 | 1/2001 | KenKnight et al. | |
| 6,253,102 B1 | 6/2001 | Hsu et al. | |
| 6,304,773 B1 | 10/2001 | Taylor et al. | |
| 6,456,881 B1 | 9/2002 | Bornzin | |

(Continued)

FOREIGN PATENT DOCUMENTS

EP  1123716  8/2001

(Continued)

*Primary Examiner*—Angela D. Sykes
*Assistant Examiner*—Alyssa M. Alter
(74) *Attorney, Agent, or Firm*—Schwegman, Lundberg & Woessner, P.A.

(57) ABSTRACT

A system and method for verifying capture of the heart by one or more pacing pulses using an electrogram morphology-based technique. Capture is determined by comparing an evoked response electrogram recorded during a paced cycle with a template waveform representing a paced cycle in which capture is achieved. The comparison is facilitated and made more accurate by selecting a sensing vector in which an evoked response electrogram in which no capture occurs is most dissimilar to the template.

26 Claims, 12 Drawing Sheets

U.S. PATENT DOCUMENTS

| | | |
|---|---|---|
| 6,512,953 B2 * | 1/2003 | Florio et al. .................. 607/28 |
| 6,609,023 B1 | 8/2003 | Fischell et al. |
| 6,697,673 B1 * | 2/2004 | Lu .............................. 607/28 |
| 6,738,669 B1 | 5/2004 | Sloman et al. |
| 6,748,274 B2 | 6/2004 | Levine et al. |
| 6,760,622 B2 * | 7/2004 | Helland et al. ................. 607/9 |
| 6,829,505 B2 | 12/2004 | Kramer et al. |
| 6,904,321 B1 | 6/2005 | Bornzin et al. |
| 7,177,689 B2 | 2/2007 | Ternes et al. |
| 2001/0049542 A1 | 12/2001 | Florio et al. |
| 2001/0049543 A1 | 12/2001 | Kroll |
| 2002/0193696 A1 | 12/2002 | Hsu et al. |
| 2003/0083710 A1 | 5/2003 | Ternes et al. |
| 2003/0083711 A1 | 5/2003 | Yonce et al. |
| 2004/0088018 A1 * | 5/2004 | Sawchuk et al. .............. 607/27 |
| 2004/0158165 A1 | 8/2004 | Yonce et al. |
| 2004/0158293 A1 | 8/2004 | Yonce et al. |
| 2005/0038478 A1 * | 2/2005 | Klepfer et al. ................. 607/9 |

FOREIGN PATENT DOCUMENTS

| | | |
|---|---|---|
| EP | 1155711 | 11/2001 |
| WO | WO-03020366 A1 | 3/2003 |
| WO | WO-03037428 A2 | 5/2003 |
| WO | WO-2004026398 A1 | 4/2004 |
| WO | WO-2005053792 A1 | 6/2005 |

* cited by examiner

AUTOMATIC SENSING VECTOR SELECTION FOR MORPHOLOGY-BASED CAPTURE VERIFICATION

FIELD OF THE INVENTION

This invention pertains to cardiac pacemakers and, in particular, to systems and methods for ascertaining the performance of the device and adjusting pacing parameters accordingly.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion/defibrillation.) Pacemakers typically have a programmable electronic controller that causes the pacing pulses to be output in response to lapsed time intervals and sensed electrical activity (i.e., intrinsic heart beats). Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit. If functioning properly, the pacemaker in this manner makes up for a heart's inability to pace itself at an appropriate rhythm.

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration. The minimum pacing pulse energy necessary to achieve capture by a particular pacing channel is referred to as the capture threshold. Programmable pacemakers enable the amplitude and pulse width of pacing pulses to be adjusted, along with other parameters. It is common practice to determine the capture threshold by initially pacing with a high energy to ensure capture and then progressively lowering the pacing pulse energy during a sequence of cardiac cycles until capture is no longer achieved. The pacing pulse energy can then be adjusted to an appropriate value in accordance with the determined capture threshold by setting it equal to the capture threshold plus a specified safety margin.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting an evoked atrial or ventricular depolarization that exceeds a specified value (i.e., corresponding to an evoked P-wave or evoked R-wave, respectively, on a surface electrocardiogram or their equivalents in an internal electrogram), the pacemaker is able to detect whether the pacing pulse (A-pulse or V-pulse) was effective in capturing the heart, that is, causing a contraction in the respective heart chamber. Capture verification can be performed in the clinical setting, with the clinician then adjusting pacing parameters so that the heart is reliably paced. The pacemaker itself, however, may be capable of verifying capture so that loss of capture can be detected when it occurs with pacing parameters then adjusted automatically, a function known as autocapture. (See, e.g., U.S. Pat. No. 6,169,921 issued to KenKnight, et. al. and presently assigned to Cardiac Pacemakers, Inc.) An autocapture function provides the pacemaker with extended longevity, greater ease of use, and greater patient safety.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses in a manner that results in a coordinated contraction of both atria and both ventricles. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output. The resulting diminishment in cardiac output may be significant in a patient with congestive heart failure (CHF) whose cardiac output is already compromised. Intraventricular and/or interventricular conduction defects can also be a cause of CHF in some patients. In order to treat these problems, pacemakers have been developed which provide electrical pacing stimulation to one or both of the atria and/or ventricles during a cardiac cycle in an attempt to improve the coordination of atrial and/or ventricular contractions, termed cardiac resynchronization therapy. To optimize the cardiac output for some heart failure patients, for example, the right and left ventricles are paced synchronously with a determined time offset, termed biventricular pacing.

Multi-site resynchronization pacing, however, is problematic for conventional capture verification methods based upon evoked response detection as described above. In biventricular pacing, for example, the proximity in time of resynchronization paces to the left and right ventricles may prevent an evoked response caused by the first pace from being distinguished from the second pace. In addition, the second pace could interfere with evoked response sensing when the evoked response from the first pace occurs within an amplifier blanking interval initiated by the second pace.

SUMMARY OF THE INVENTION

A depolarization waveform, such as a surface electrocardiogram (ECG) or internal electrogram, recorded during a paced event that achieves capture exhibits morphological differences from that recorded during a paced event that fails to achieve capture. Also, when multiple pacing pulses are delivered to either the atria or the ventricles during a cardiac cycle, the morphology of the depolarization waveform that results is affected if even one of the pacing pulses fails to achieve capture. In accordance with the invention, capture of the heart by a pacing pulse is verified by comparing an evoked response or test depolarization waveform recorded during the paced event with a reference template waveform representing capture of the heart by a similarly delivered pacing pulse. The comparison may be done by cross-correlating the reference template and test waveforms so that loss of the capture is detected when the two waveforms become uncorrelated. In a multi-site pacing situation, template waveforms representing capture by each pace individually and by all of the paces collectively can be used to determine which pace failed to achieve capture and to simplify the determination of capture thresholds for each pacing site.

In a situation where first and second pacing pulses are output to either the atria or ventricles during a cardiac cycle, capture by both pacing pulses may be detected if a recorded evoked response waveform is highly correlated with a template waveform representing capture by both pacing pulses and, additionally, is correlated with template waveforms representing capture by only the first pacing pulse and capture by only the second pacing pulse only to a specified extent. In an exemplary embodiment, biventricular capture is detected if the evoked response highly correlates with a template waveform representing biventricular capture and correlates with templates representing right ventricular and left ventricular capture to roughly the same extent as does the biventricular capture template.

In the above-described morphology-based capture verification techniques, a recorded evoked response waveform is compared with one or more template waveforms in order to determine whether or not capture by one or more pacing pulses has occurred. Capture determination by these techniques depends upon there being some degree of dissimilarity between the template representing capture and a non-capturing evoked response waveform. The degree of dissimilarity between the two waveforms will generally vary with the particular sensing vector used to generate the template and evoked response electrograms. In accordance with another aspect of the invention, a sensing vector for generating template and evoked response waveforms is selected by comparing electrograms generated by capturing and non-capturing pacing pulses for a number of different sensing vectors and selecting the one which results in the greatest degree of dissimilarity. In a biventricular pacing example, an electrogram generated during biventricular capture is cross-correlated with an electrogram generated during right ventricular-only capture for a plurality of sensing vectors with the optimum sensing vector chosen as the one for which the two waveforms are least correlated.

DETAILED DESCRIPTION

The present invention relates to a system and method for verifying capture by a cardiac pacemaker in which the morphology of an evoked response electrogram waveform recorded during a paced cardiac cycle is compared with that of a template waveform representing a paced cycle which has achieved capture. Capture is deemed to have occurred if the comparison shows a similarity between the two waveforms above a specified threshold. As detailed below, one way in which the comparison may be made is by performing a cross-correlation between the evoked response and template waveforms. In one embodiment, the method is implemented as a system incorporating an implantable pacemaker and an external programmer or similar device capable of communicating with the pacemaker over a wireless telemetry link. The processing of the evoked response and template waveforms for verifying capture may be performed entirely by the external programmer, by the implantable pacemaker, or shared between the two devices. The template and evoked response waveforms may be intracardiac electrograms or leadless electrocardiograms (ECG's) generated by a sensing channel of the pacemaker or may be surface ECG's recorded by the external programmer. In the former case, intracardiac electrograms or wireless ECG's may be transmitted to the external programmer by the pacemaker over the telemetry link. In another embodiment, the system for capture verification is entirely implemented in the pacemaker. In either embodiment, morphology-based capture verification may be used as part of an automatic or manual procedure for determining pacing thresholds and setting pacing pulse energies accordingly.

Another aspect of the invention involves analyzing the morphologies of evoked response waveforms recorded with different sensing vectors during paced cycles in which capture has and has not occurred. By this analysis, the best sensing vector for performing morphology-based capture verification may be selected.

a. Hardware Platform

Figure 1:
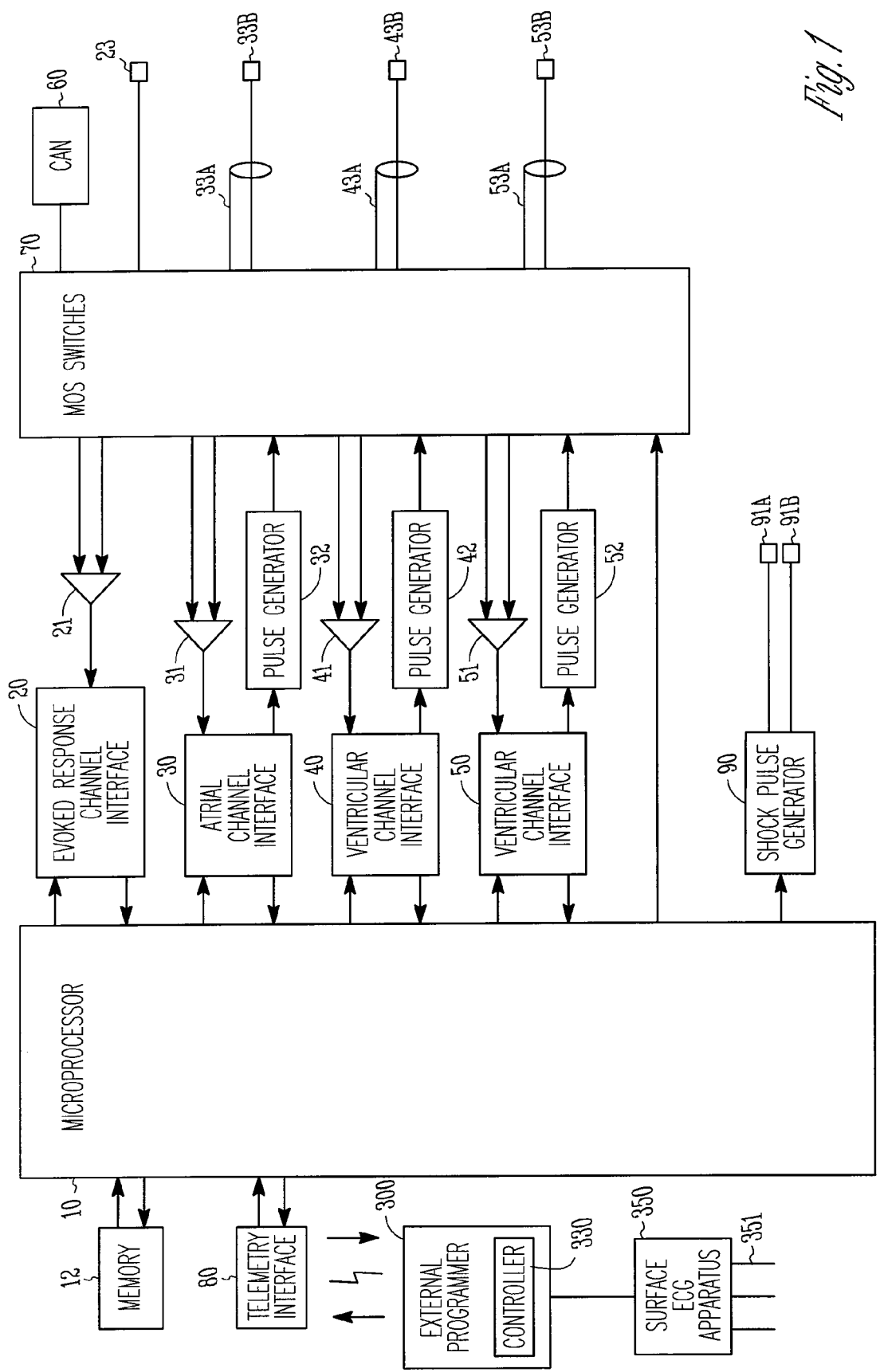
FIG. 1 is a block diagram of a multi-site pacemaker.

The present invention may be used by pacemakers having a number of different pacing configurations, including single-chamber pacing configurations and multi-site pacing configurations for delivering various types of resynchronization therapy where a pace is delivered to each of the paired atria and/or ventricles during a cardiac cycle or where multiple paces are delivered to a single chamber. For illustrative purposes, however, a the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1.

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with a controller 330 that can interrogate the pacemaker and receive stored data as well as adjust the operating parameters of the pacemaker. The external programmer may also incorporate a surface ECG apparatus 350 for recording surface ECG's generated from leads 351 attached to the patient's body surface. As the term is used herein, an electrogram should be taken to refer to either an intracardiac electrogram or a subcutaneous ECG generated by a sensing channel of an implantable device, or to a surface ECG.

The pacemaker has an atrial sensing/pacing channel comprising ring electrode 33a, tip electrode 33b, sense amplifier 31, pulse generator 32, and an atrial channel interface 30 which communicates bidirectionally with a port of microprocessor 10. The device also has two ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. A shock channel is also provided comprising a shock pulse generator 90 and shock electrodes 91a and 91b that enables the device to deliver a defibrillation shock to the heart when fibrillation or other tachyarrhythmia is detected. The pacemaker also has an evoked response sensing channel that comprises an evoked response channel interface 20 and a sense amplifier 21 that has its differential inputs connected to a unipolar electrode 23 and to the device housing or can 60 through the switching network 70. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be transmitted via the telemetry link 80 to the external programmer 300 or stored for later transmission. The patient's cardiac activity may thus be observed in real-time or over a selected historical period.

The electrical response of the heart to a pacing pulse is referred to as an evoked response. If the evoked response indicates that a propagating wave of depolarization has resulted from the pacing pulse, it evidences that the paced chamber has responded appropriately and contracted. An evoked response can therefore be used to verify that the pace has achieved capture of the heart. In accordance with the invention, an electrogram can also be recorded of an evoked response to a pace and used to determine if capture is achieved by comparing the recorded electrogram with a template electrogram representing capture of the heart by a similarly delivered pace. An evoked response sensing channel for recording an electrogram can be a sensing channel normally used for other purposes or can be a sensing channel dedicated to sensing evoked responses. It is preferable to record the electrogram with a unipolar electrode that "sees" a larger volume of the myocardium as a wave of electrical activity spreads than a bipolar electrode. In the embodiment illustrated in FIG. 1, the atrial and ventricular sensing pacing channels utilize bipolar electrodes, and a dedicated evoked response sensing channel is provided with a unipolar electrode. Alternate embodiments may employ unipolar electrodes in the atrial and/or ventricular sensing/pacing channels, in which case unipolar sensing of an evoked response may be performed with those channels instead of a dedicated channel. The evoked response sensing channel may also be implemented by the shock channel wherein the shock leads normally used for delivering defibrillation shocks to the heart are switched to a sensing amplifier by the switch matrix 70. The device may also record subcutaneous ECG's during evoked responses using electrodes on the surface of the device housing or otherwise subcutaneously disposed.

b. Template-Based Capture Verification and Threshold Determination

In accordance with the invention, capture of heart by multiple pacing pulses delivered to the atria and/or ventricles during a cardiac cycle is verified by recording an evoked response waveform during the pacing cycle, also referred to herein as a test depolarization waveform, and comparing the recorded waveform with a template depolarization waveform representing capture of the heart by at least one pacing pulse. Although the method described herein for capture verification and threshold determination may be applied to any multi-site pacing configuration, the following detailed explanation and description of specific embodiments will be confined to a biventricular pacing configuration where both ventricles are paced during a cardiac cycle separated by a programmed offset.

Figure 2A:
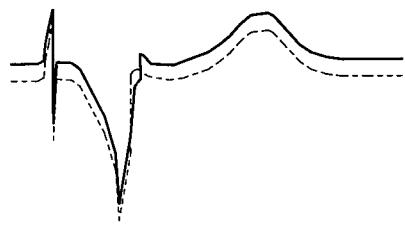
FIGS. 2A and 2B illustrates an ECG recorded after a pace and a template ECG.
Figure 2B:
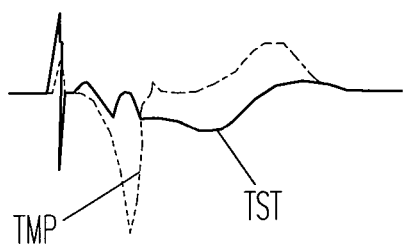

Delivery of multiple paces to the ventricles during a cardiac cycle changes the pattern of the resulting depolarization as compared with the pattern that results from a single ventricular pace. This difference appears as a QRS wave morphology change in a recorded depolarization waveform such as a surface ECG or electrogram that senses the time-varying net dipole vector produced by the depolarization. A reference template waveform can be created by recording a ventricular ECG or electrogram during a biventricular pacing cycle that is known to achieve capture with both pacing pulses. Presence or absence of capture for a given pace can then be determined by comparing the template waveform with a test depolarization waveform recorded during the pace. FIG. 2A shows an example of a template ECG waveform TMP and a test ECG waveform TST that match, while FIG. 2B show test and template waveforms that are morphologically different because of a failure to achieve capture by one of the pacing pulses.

In an exemplary implementation, the degree of similarity between a test waveform and a template waveform is ascertained by performing a time-domain cross-correlation between the waveforms. Loss of capture at one of the ventricular pacing sites is then indicated by a loss of correlation between the test and template waveforms. The exact correlation values that should optimally be used in deciding whether or not a test waveform and template waveform match may be selected on the basis of empiric testing as the optimum values may vary for an individual patient and/or pacemaker. Capture verification performed in this manner may be used to determine the capture threshold of a pacing channel by varying the pacing pulse energy and finding the minimum energy which results in capture.

Capture verification and threshold determination as described above may be implemented in a number of different ways. In one exemplary embodiment, a surface ECG is recorded with conventional leads during pacing by an external programmer that communicates with the implanted pacemaker via a radio telemetry link. The processor of the external programmer then performs the correlation between the test ECG and a template ECG to determine if capture is achieved by the pacing pulses. In a modification to this embodiment, rather than using surface ECGs, a test electrogram recorded by an evoked response sensing channel of the pacemaker and transmitted to the external programmer is compared with a template electrogram to verify capture. The external programmer can employ the telemetry link to adjust the pacing pulse energy in order to determine the capture threshold and then set the pacing pulse energy at an appropriate value, either under the direction of a clinician or automatically by software running in the external programmer.

In another embodiment, the controller of the pacemaker is programmed to verify capture by comparing the test electrogram with the template electrogram and to determine the capture threshold by varying the pacing pulse energy, either autonomously at selected times or in accordance with instructions received over the telemetry link. The controller may then be further programmed to automatically set the pacing pulse energy in accordance with the determined capture threshold. Determination of the capture threshold may be performed automatically on a periodic basis or at the direction of a clinician communicating with an external programmer. The controller may also be programmed to verify capture by pacing pulses on a beat-to-beat basis. If a loss of capture is detected, the controller can then perform a capture threshold determination and adjust the pacing pulse energy as appropriate. Loss of capture events may also be logged in the memory of the controller for later transmission to an external programmer.

Figure 3A:
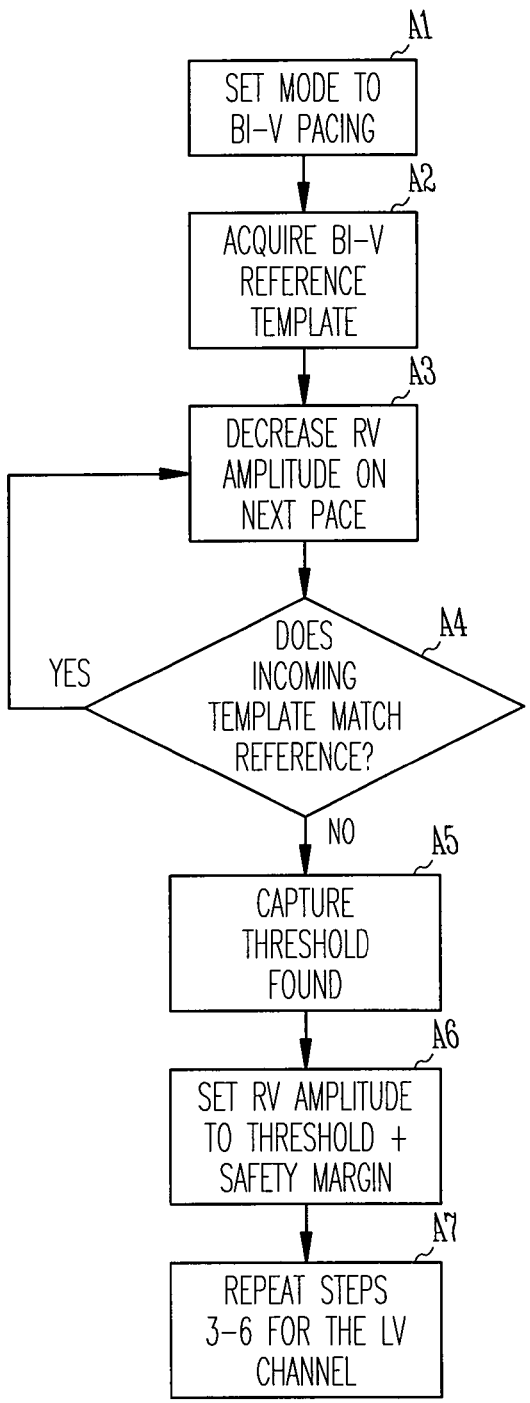
FIGS. 3A and 3B illustrate exemplary embodiments of algorithms for capture threshold determination.

FIG. 3A illustrates an exemplary procedure for determining the threshold voltage of the right and left ventricular pacing channels (referred to as RV and LV, respectively) in a bi-ventricular pacemaker using ECG or electrogram waveforms. The auto-threshold algorithm begins at steps A1 and A2 by pacing both chambers of the heart and recording an ECG or electrogram to create a biventricular (Bi-V) template waveform that is to be used as a reference. The pacing pulse amplitude for both ventricles is set at a relatively high value to ensure capture during acquisition of the biventricular template waveform. After the template waveform is obtained, the system decreases one of the pacing amplitudes at step A3, in this case the RV pacing amplitude, before the next pace. The RV pace triggers the recording of an incoming ECG or electrogram following the pace that is to be used as the test waveform in verifying capture. A cross correlation is performed between the template waveform and the test waveform at step A4. If the waveforms correlate well, then both ventricular pacing channels are assumed to have achieved capture and step A3 is repeated to decrease the RV pacing amplitude. If loss of correlation is detected at step A4, then the RV pacing amplitude is assumed to have dropped below the threshold voltage. The capture threshold is then determined at step A5 to be the RV pacing amplitude before the decrease at step A3. The system then sets the RV pacing pulse amplitude to the threshold voltage plus some safety factor at step A6. Steps A3 through A6 are then repeated for the LV pacing channel as indicated by step A7 in order find the LV capture threshold and set the LV pacing amplitude.

In single-site pacing systems utilizing capture verification, it is desirable to quickly pace the heart once a loss of capture occurs. This becomes especially important with pacing-dependent patients in order to maintain cardiac activity. Often the delay associated with the external programmer ECG and with the telemetry systems used for communication between the external programmer and the pacemaker can prohibit immediate safety pacing. Note, however, that the bi-ventricular auto-threshold algorithm presented above inherently includes a safety back-up pace with the additional ventricular pacing channel. Once one channel loses capture, the other still causes contraction of the ventricles, maintaining ventricular function. Because of the safety provided by two ventricular pacing sites, the auto-threshold algorithm could also start with one output high and increase the other from a sub-threshold voltage. (This is undesirable for more than a few cycles, of course, since the benefits of resynchronization therapy are lost if biventricular capture does not occur.) For example, a template can be created for RV-only pacing. The LV pacing amplitude then increases from a sub-threshold voltage until the system detects Bi-V pacing. This flexibility thus facilitates the use of more efficient search algorithms to speed convergence to the proper threshold value.

Figure 3B:
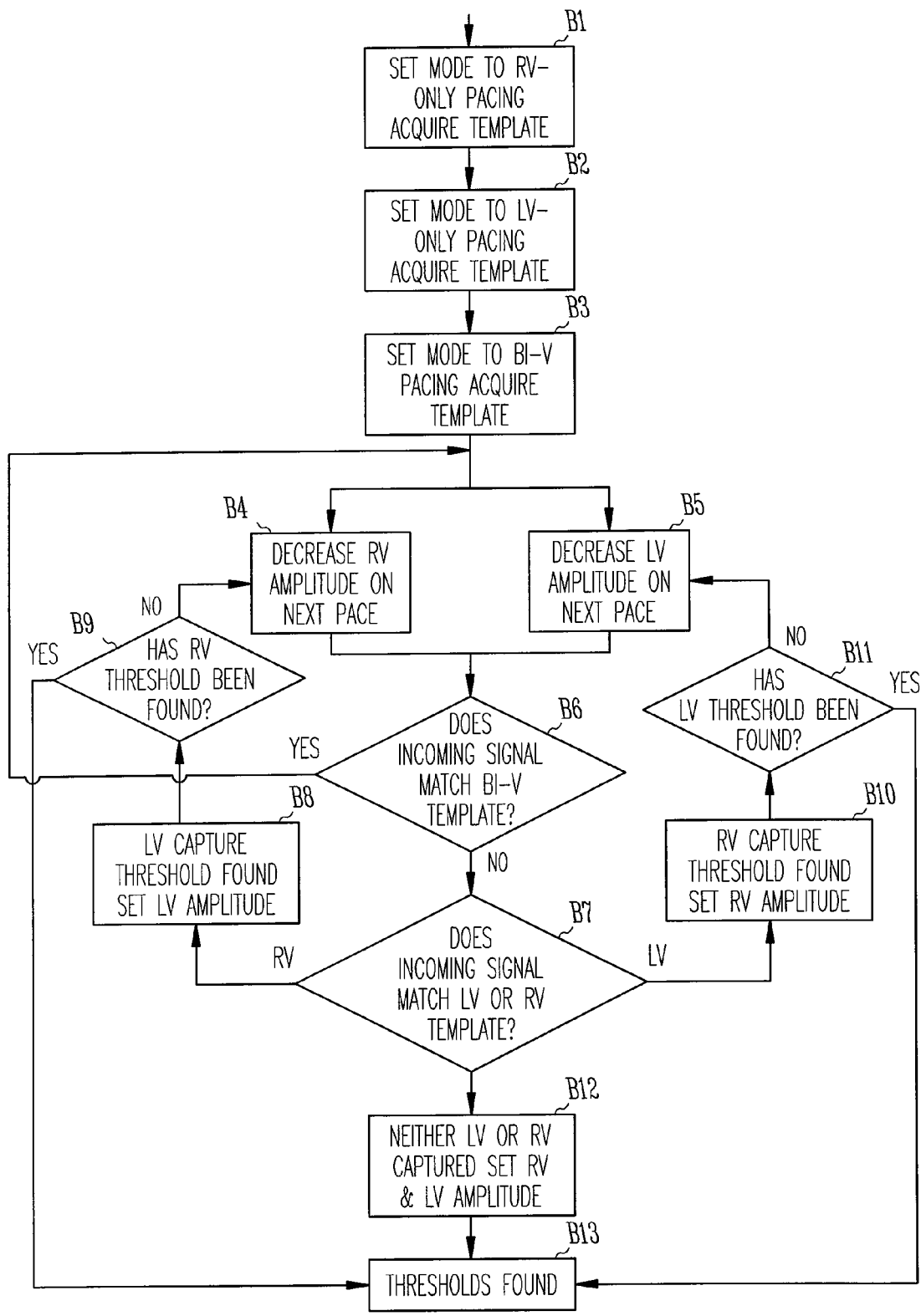

Another exemplary procedure is illustrated by FIG. 3B that decreases the total time of the auto-threshold algorithm by determining the LV and RV capture thresholds simultaneously. The algorithm first acquires templates in the RV-only, LV-only, and Bi-V pacing configurations at steps B1, B2, and B3. After creation of the templates, the system begins decreasing RV and LV pacing amplitudes simultaneously with each pace as indicated by steps B4 and B5, respectively. Similar to the previous algorithm, the RV pace triggers the creation of a test waveform. Cross correlations are then performed between the test waveform and the three templates. If a high correlation exists between the test waveform and the Bi-V template at step B6, both pace amplitudes are assumed to still be above the capture threshold value and the algorithm returns to steps B4 and B5. Otherwise cross-correlations between the test waveform and the RV-only and LV-only templates are performed at step B7. If a high correlation exists between the LV-only template and the test waveform, then the RV pacing amplitude has dropped below the threshold voltage, and the RV capture threshold is found at step B10. Likewise, a high correlation between the test waveform and the RV-only template indicates that the LV pace amplitude has dropped below the threshold voltage, and the LV capture threshold is found at step B8. If a capture threshold is found for a pacing channel at either step B8 or B10, steps B9 and B11 then test whether a capture threshold for the other pacing channel has been found so that the procedure can either end at step B13 or return to step B4 or B5. If the system indicates no correlation between the test waveform and any of the templates, then both pacing channels have dropped below the threshold value. The capture thresholds for both pacing channels are then found so that the pacing thresholds can be adjusted accordingly as indicated by steps B12 and B13.

Figure 4A:
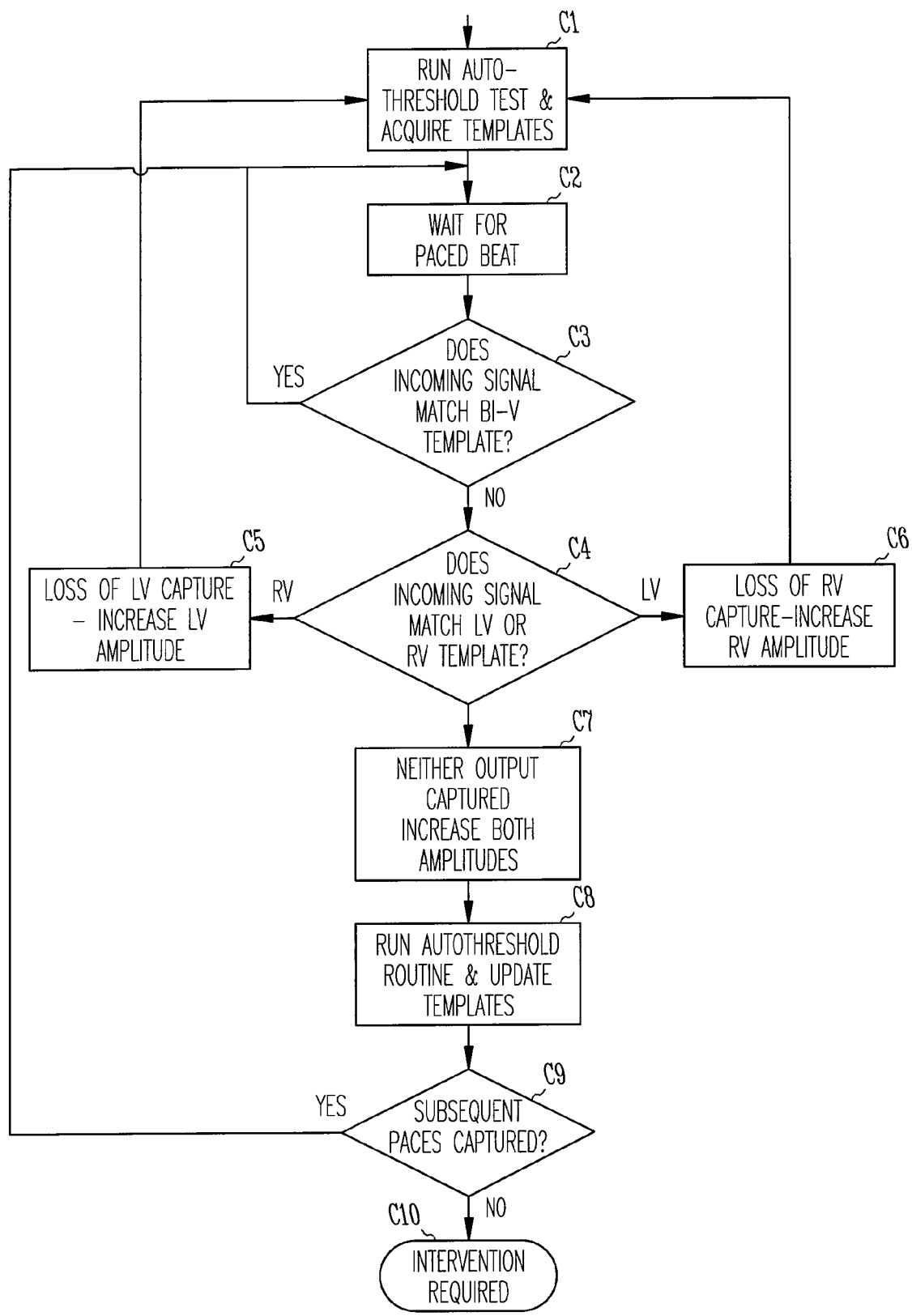
FIGS. 4A and 4B illustrate exemplary embodiments of an auto-capture algorithm.
Figure 4B:
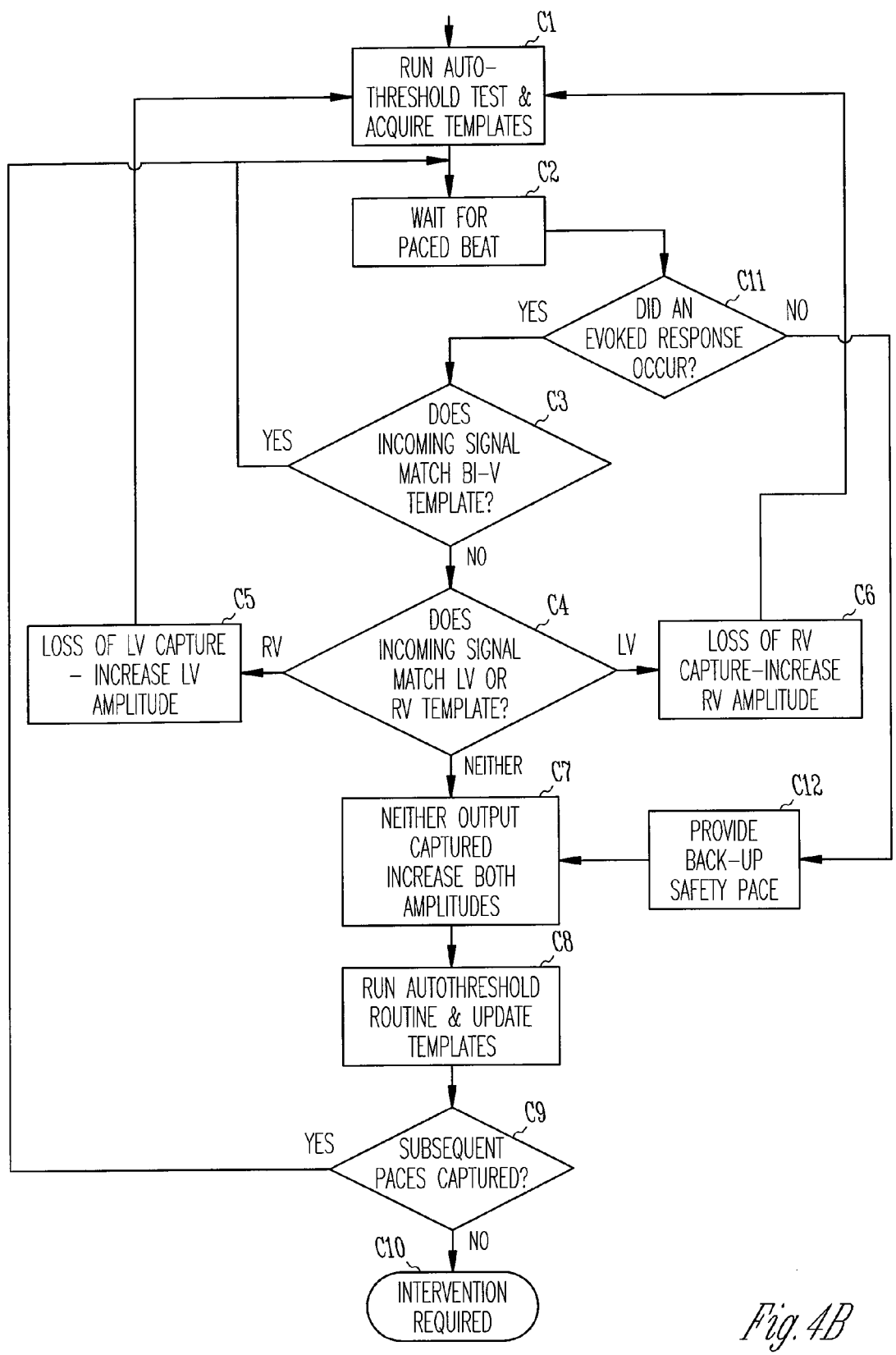

The auto-threshold algorithms illustrated in FIGS. 3A and 3B may be performed by either the pacemaker controller or the processor of an external programmer when it is desired to determine the capture thresholds for the RV and LV pacing channels and set the pacing amplitudes accordingly. As noted above, however, capture verification by cross-correlating template and test waveforms may also be performed on a beat-to-beat basis by the pacemaker controller to provide an ambulatory auto-capture function. FIGS. 4A and 4B illustrate exemplary algorithms for implementing auto-capture in which a capture verification test is performed with each pace.

Referring first to FIG. 4A, the controller performs an auto-threshold algorithm at step C1 in which templates are acquired in the RV-only, LV-only, and Bi-V pacing configurations and capture thresholds are determined for the LV and RV pacing channels so that the pacing pulse amplitudes can be set accordingly. The device then operates normally while the algorithm waits for a paced beat at step C2. At step C3, an incoming signal is used as a test waveform and cross-correlated with the Bi-V template to ascertain if both the RV and LV pacing pulses have achieved capture. If the Bi-V template and test waveforms are highly correlated, capture is assumed, and the algorithm loops back to step C2. If a lack of correlation between the test waveform and the Bi-V template is found, the algorithm separately cross-correlates the test waveform with the LV and RV templates at step C4. If the test waveform matches the RV template, lack of capture in the LV pacing channel is assumed. The LV pacing pulse amplitude is then increased at step C5, and the algorithm returns to step C1 so that updated templates can be acquired and an updated capture threshold determined. Similarly, if the test waveform matches the LV template, the RV pacing pulse amplitude is increased at step C6, and the algorithm returns to step C1. If neither the RV nor the LV paces have achieved capture as indicated by a lack of correlation between the test waveform and the two templates, both the RV and LV pacing amplitudes are increased at step C7. An auto-threshold algorithm is then performed at step C8, with the templates and capture thresholds updated and the pacing pulse amplitudes set accordingly. A capture verification test is performed at step C9 as the device operates with the updated pacing pulse amplitudes. If capture is achieved, the algorithm returns to the capture verification loop of steps C2 and C3. If subsequent paces still fail to achieve capture, it can be assumed that the lack of capture is due to factors other than pacing pulse energy such as the occurrence of fusion events (i.e., a capture by a pacing pulse coincident with an intrinsic contraction), difficulties in obtaining reference templates, or the occurrence of a malfunction in the pacemaker or lead system. An indication that further intervention is required is then logged in memory at step C10 which can be communicated to a clinician during the next communications session with an external programmer.

The ambulatory auto-capture algorithm presented in FIG. 4A relies on the inherent safety of having multiple ventricular pacing sites in the ventricle. In the event that one chamber loses capture, there is a low probability that the other chamber will simultaneously lose capture. Nonetheless, there is a possibility that the pacemaker could lose capture on both chambers simultaneously. When capture of the ventricles does not occur, it is desirable to provide a back-up safety pace to the right ventricle to immediately provide pacing therapy to prevent the patient from feeling light headed or loosing consciousness. Depending upon the particular implementation, the template cross-correlation algorithms presented here could take greater than 100 ms to accurately identify pacing activity. This is usually too long of a delay to deliver a safety pace. Further, if a fusion event occurs, the device must prevent pacing into a t-wave, so it must again react quickly if a safety pace is to be delivered. FIG. 4B is a flowchart diagram showing an ambulatory auto-capture algorithm that uses a traditional evoked response comparator in addition to template recognition. Steps C1 through C10 in FIG. 4B are identical to those described above with reference to FIG. 4A. After each paced beat, however, the algorithm also tests for capture at step C11 with an evoked response comparator that looks for any evoked response above a specified threshold following a pace. If any evoked response occurs from the ventricles, then some cardiac ventricular activity is assumed to have occurred, and the algorithm proceeds to step C3 to perform the template correlations and determine which chamber or chambers were captured. If no evoked response occurs following a pace, on the other hand, then the algorithm applies a safety pace to the right ventricle at step C12 and then proceeds as if neither pacing pulse captured by going to step C7. In this manner, the patient receives pacing therapy without a noticeable delay.

In the capture verification methods described above, a test depolarization waveform, such as an electrogram or ECG signal, is recorded and compared with one or more template waveforms. In certain implementations, this may involve the processor of the pacemaker or external programmer storing samples of a segment of the test waveform in memory and then performing the cross-correlation operation with corresponding samples of a template waveform. Recording and correlation of the test waveform with a template, however, may also be implemented by passing samples of the incoming electrogram or ECG signal through a finite impulse filter that performs the cross-correlation operation. In that case, the filter may be a matched filter having an impulse response equal to a time-reversed version of a template waveform. The test waveform is thus cross-correlated with a template waveform represented by the filter coefficients of the matched filter. Such a matched filter may be provided for each of the RV-only, LV-only, and BiV template waveforms and may be implemented either in code executed by the controller or as one or more dedicated hardware components.

Capture verification by comparing a test or evoked response depolarization waveform with a template has been described above in the context of multi-site pacing where either one or both of the paired atria or one or both of the paired ventricles are paced with multiple paces during a cardiac cycle. It should also be appreciated that a test depolarization waveform, such as an electrogram from an evoked response sensing channel, can be recorded during delivery of a single pacing pulse and then compared with a template waveform representing single-site capture of the heart by a pacing pulse in order to determine if capture has been achieved by the delivered pacing pulse.

c. Template Acquisition

Reliable determination of whether a pacing pulse has achieved capture by comparison of a test depolarization waveform with a reference template as described above requires that the reference template accurately reflect the particular evoked response being looked for. Simply recording a depolarization waveform during a pacing cycle with pulse energies known to be sufficient to achieve capture, however, does not guarantee a satisfactory reference template because of the possibility of PVC's, fusion events, or external noise. A PVC or premature ventricular contraction occurs when an intrinsic ventricular contraction occurs independently from excitation originating from the SA node. A fusion event is the occurrence of an intrinsic contraction coincident with capture of the heart by a pacing pulse. External noise may be produced by any source of electromagnetic energy such as a telemetry transmission from an external programmer. If any of these events occur while a reference template is being recorded, the resulting template will be a corrupted waveform that will not correlate with the desired capture event and will lead to erroneous results during an autothreshold routine. In order to avoid these problems and construct accurate templates, a template acquisition algorithm may be employed that takes advantage of the anomalous nature of the corrupting events.

Figure 5:
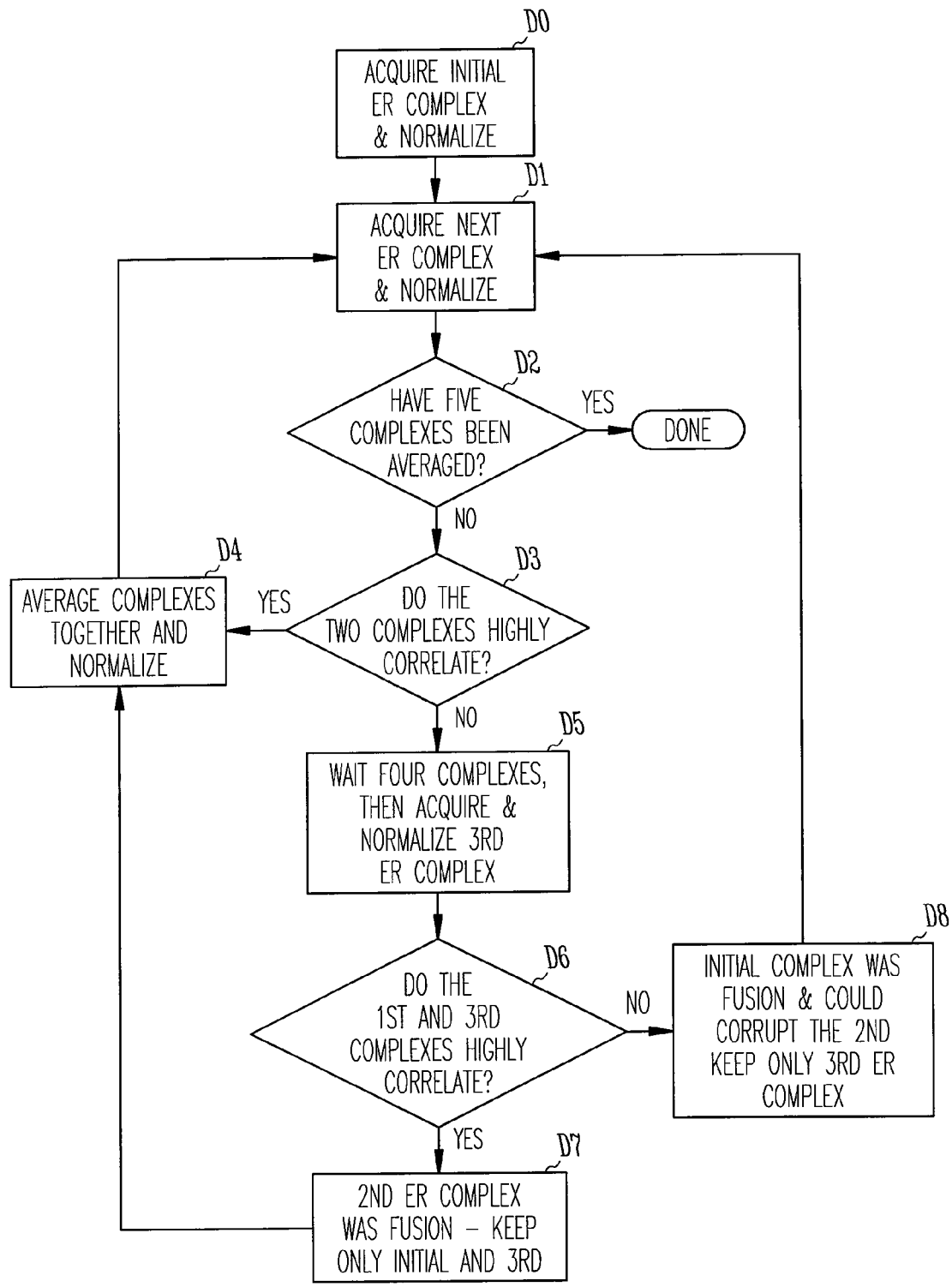
FIG. 5 illustrates an exemplary template acquisition algorithm.

FIG. 5 shows a flowchart of an exemplary template acquisition routine. In order to avoid recording fusion as well as other anomalous events as reference templates, the routine calculates the correlation coefficient (CC) of successive evoked responses and decides which responses to keep as templates based upon the CC. Initially, two evoked responses are collected and normalized at steps D0 and D1. The correlation between the two normalized evoked responses is calculated. If the two waveforms are found to highly correlate at step D3, then they are averaged together and the average is again normalized at step D4. The algorithm then returns to step D1 to acquire another evoked response. This process continues until five evoked responses are averaged together as tested for at step D2. If, on the other hand, the two complexes do not highly correlate at step D3, then the algorithm waits for several beats and then collects a third evoked response at step D5. Clinical data has indicated that PVCs or telemetry programming can affect the morphology of an evoked response for several beats. Waiting several beats thus allows any possible perturbation of the evoked response to complete before continuing. If the first and third evoked responses highly correlate at step D6, the second evoked response is regarded as noise or fusion. The second evoked response is then thrown out at step D7, and the first and third evoked responses are averaged at step D4. If the first and the third evoke responses do not highly correlate at step D6, then the initial complex is assumed to have been fusion. Because of the turbulence that can last several beats following a PVC or fusion, the first fusion event could have affected the second evoked response. Therefore, the algorithm keeps only the third evoked response at step D8 and begins again at step D1.

d. Discriminating Between Biventricular and Right-Ventricular Capture

Figure 6:
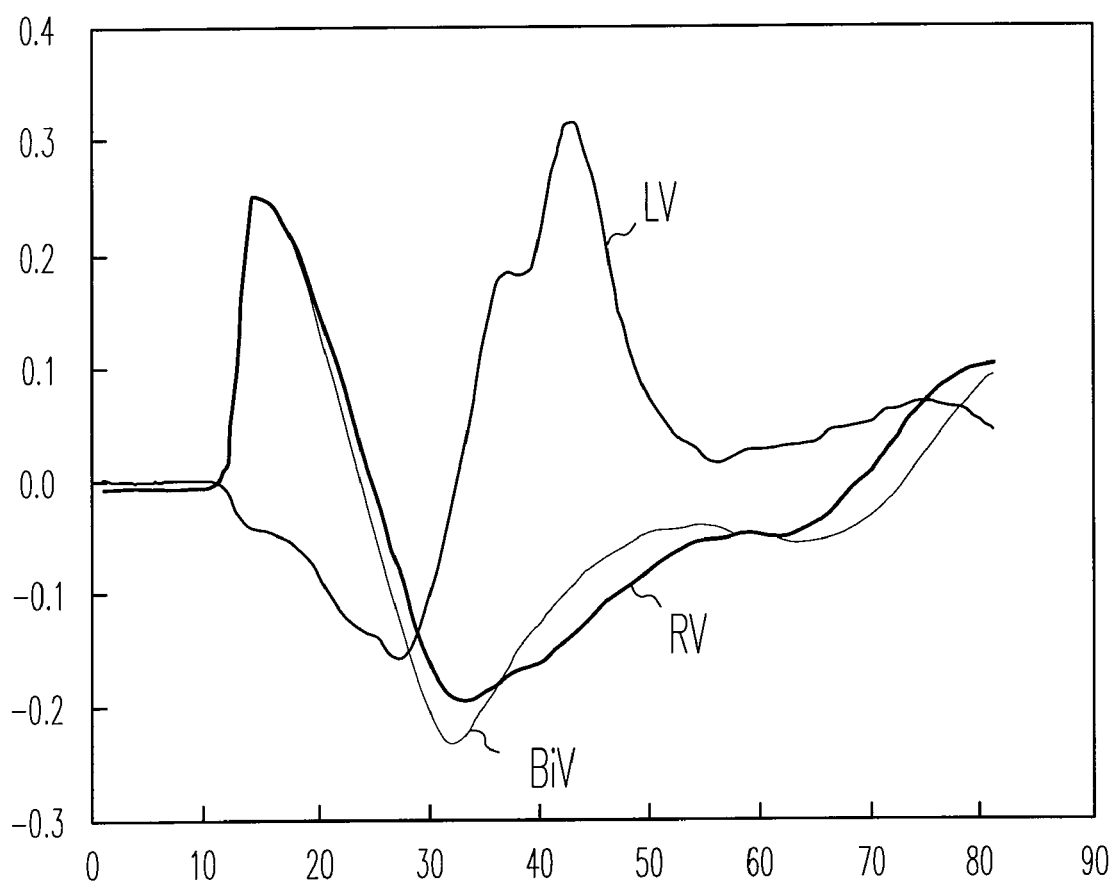
FIG. 6 shows examples of BiV, RV, and LV paced evoked responses.

FIG. 6 shows an example of BiV, RV, and LV paced evoked responses, each 400 ms in length, taken from one subject with the shock channel used as the evoked response sensing channel. As can be seen, the LV and BiV pacing cases produce great differences in the evoked responses. Considering that the shock electrodes are located in the right side of the heart, the sensing vector will be sensitive to a lack of activity from the right ventricle. This, of course, would also be true for any evoked response sensing channel with sensing electrodes on the right side of the heart. Conversely, the BiV and RV evoked responses display a high degree of similarity, correlating more than 95% in this particular subject. This is to be expected since both the RV and BiV paces will similarly contract the right ventricle tissue early in the r-wave complex. Much of the right ventricular cells are placed in refractory from the RV or BiV pace, allowing little further activity once the wavefront arrives from the left ventricular pace. Additionally, the magnitude of the signals from the right ventricle can swamp any far-field signals from the left side.

The high similarity of the BiV and RV templates in this example suggest that standard cross correlation techniques may not be sufficient for distinguishing between BiV and RV capture when the shock channel, or any sensing channel with electrodes located on the right side of the heart, is used as the evoked response sensing channel. A secondary criterion may therefore be used to fully discriminate between BiV and RV evoked responses with a right-sided sensing vector. It has been found that the highest level of difference between two such evoked responses occurs approximately 200 ms following a pace during the s-t transition. The normalized evoked responses to BiV and RV capture with a right-sided sensing vector in a number of experimental subjects have been found to be consistent and different during this time interval. This morphology difference can be used to distinguish between the BiV and RV capture by calculating the total energy in the normalized evoked response during a sub-window interval of 200-300 ms following the pace. The acquired BiV and RV templates are first used to calculate the energy in both templates. An energy bound can then be established by taking half of the energy difference:

$$E_{limit} = \frac{E_{max} - E_{min}}{2} + E_{min}$$

where $E_{max}$ is the larger of template energies, $E_{min}$ is the lesser value, and $E_{limit}$ is the energy bound or limit value. For example, the RV template may have a greater energy in the sub-window than the BiV template. A normalized evoked response with energy above the limit would then be classified as an RV capture, while a normalized evoked response with less total energy than the limit would be denoted as a BiV capture. Conversely, if the RV template has a lesser energy in the sub-window than the BiV template, an evoked response with greater total energy than the limit would be classified as a BiV capture. It should be appreciated that the same method could be used for discriminating between BiV and LV capture in the case where the evoked response sensing channel has sensing leads located on the left side of the heart.

In the method for BiV/RV capture discrimination just described, where the BiV and RV evoked response waveforms are similar due to right-sided sensing, BiV and RV capture are distinguished by measuring the total signal energy in a particular sub-window interval following the pace. Whether or not this BiV/RV capture discrimination method is needed depends upon both the particular patient and the electrode arrangement used for sensing the evoked response. Discussed below is a template-based capture verification algorithm that, among other things, employs the BiV/RV capture discrimination method and uses additional correlation criteria to determine when the method should be used.

e. Algorithm for Enhanced Discrimination of Evoked Responses

In the capture verification algorithms discussed above with respect FIGS. 3A-B and 4A-B, capture of one or both ventricles was assumed when the evoked response waveform was sufficiently correlated with a particular template waveform. Ideally, however, a template-based capture verification algorithm would reliably distinguish between one of five events: BiV capture, RV capture, LV capture, fusion, or asystole. Also, as discussed above, simple correlation of an evoked response with template waveforms representing left-ventricular, right-ventricular, or bi-ventricular capture may not be able to reliably distinguish between biventricular capture and capture of the ventricle where the evoked response sensing electrodes are located.

Figure 7:
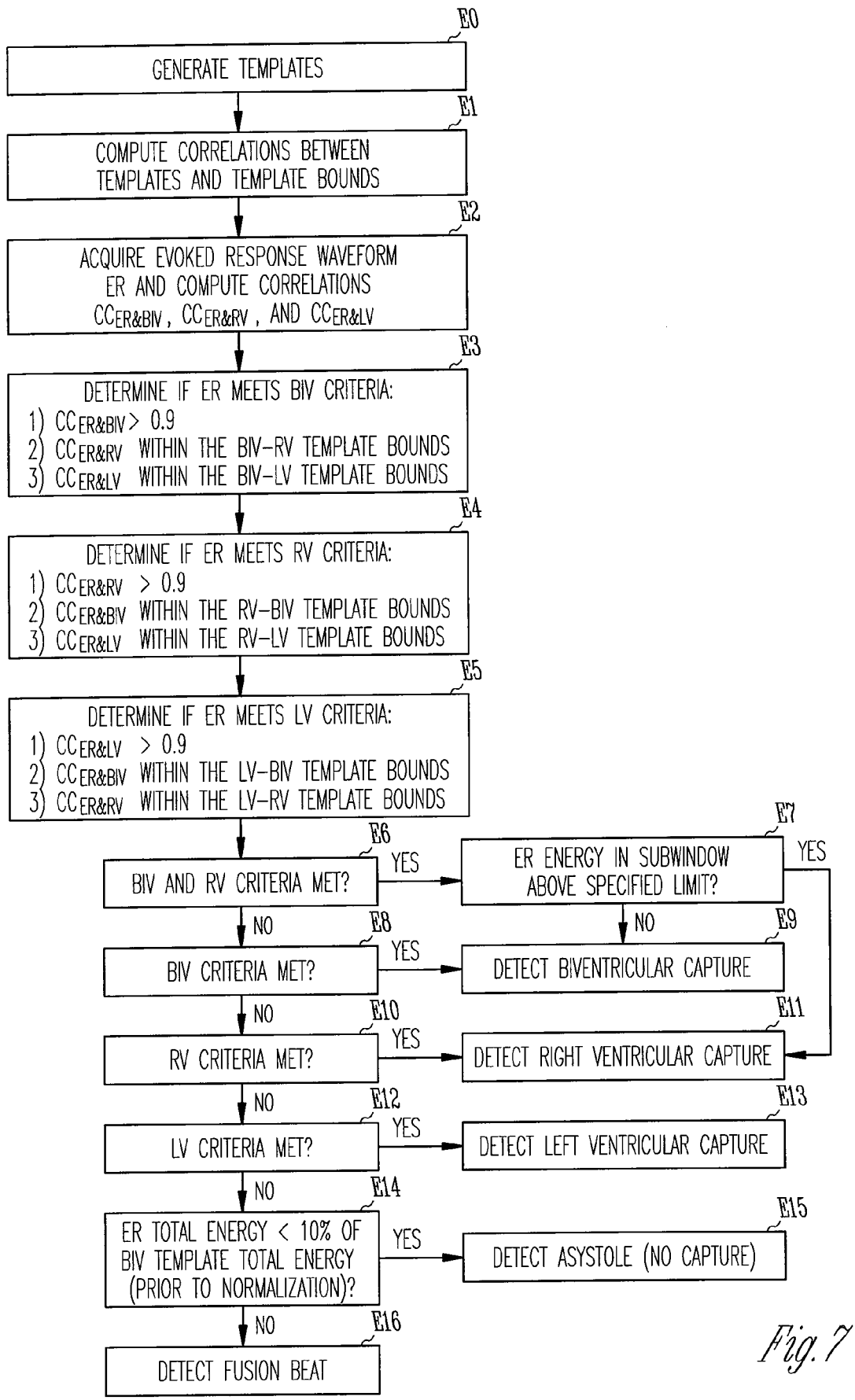
FIG. 7 illustrates an algorithm for enhanced discrimination between evoked responses.

A template-based capture verification algorithm which employs additional detection criteria to distinguish between all of the possible evoked response events is illustrated in FIG. 7. In order to add specificity to the algorithm, the evoked response waveform is correlated with template waveforms representing BiV, RV, and LV capture and is then classified according to whether it meets multiple criteria for BiV, RV, or LV capture. The multiple criteria for detecting each form of capture require not only a high degree of correlation with the template waveform representing that form of capture but also correlation values with the other template waveforms within specified ranges selected in accordance with the correlation between the different template waveforms. For example, an evoked response waveform will only be classified as meeting the criteria for BiV capture when it is highly correlated with the BiV template and correlated with the RV and LV templates to roughly the same extent as the BiV template. When an evoked response waveform meets the criteria for both BiV and RV capture, the method for BiV/RV discrimination using the signal energy in the subwindow interval discussed above is employed. If none of the capture criteria are met by the evoked response waveform, the algorithm then detects either asystole (i.e., no capture) or a fusion beat in accordance with the total signal energy in the evoked response waveform.

Referring to FIG. 7, the algorithm begins at step E0 with acquisition of templates. In order to ensure sufficient signal for a valid comparison, both the evoked response and template waveforms are recorded for 400 milliseconds following a pace. At an example sample rate of 200 Hz, an array of 80 samples constitutes each 400 ms recorded template or evoked response waveform. The algorithm generates the templates for BiV, RV, and LV capture events by pacing the heart in the appropriate pacing modes and recording the resulting waveforms. During template acquisition, the device is programmed with high pacing output voltages to ensure capture from the pacing outputs. The algorithm may also use the template acquisition routine described above with reference to FIG. 5 in order to ensure that the templates faithfully reflect the different capture events.

Figure 8:
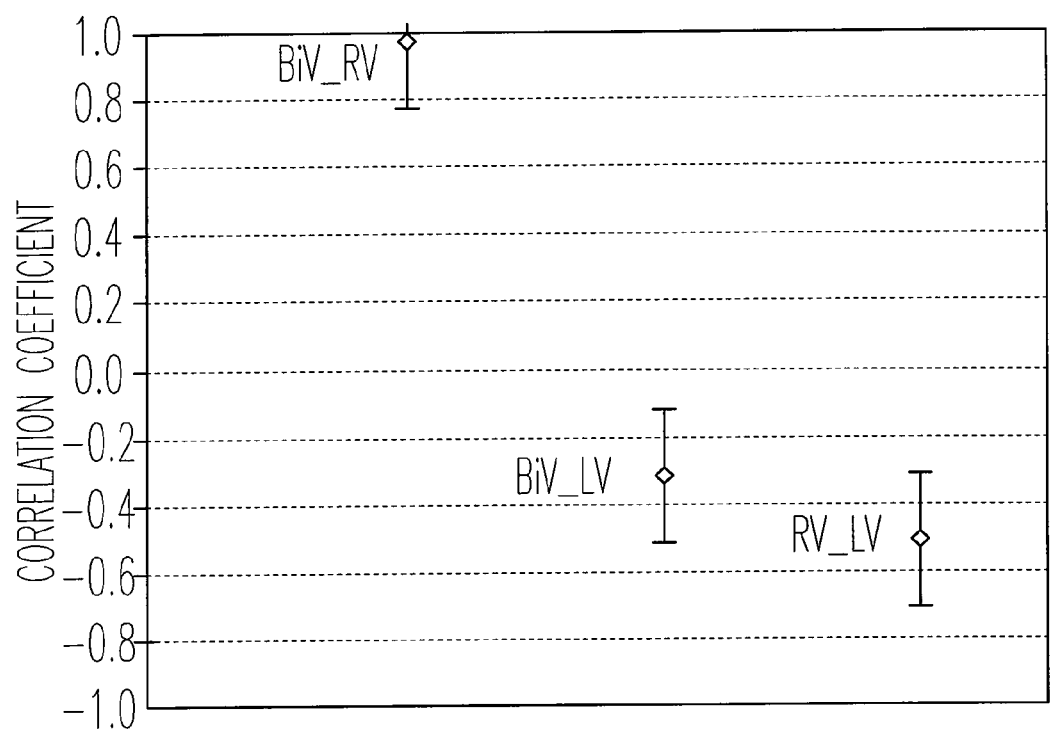
FIG. 8 shows a plot of the template correlation coefficients waveforms such as shown in FIG. 6.

Following the generation of the templates at step E0, the correlation coefficients between the templates are calculated at step E1 to measure the degree of similarity between all three templates. The correlation coefficients are calculated as follows:

$$CC = \frac{\sum_{i=1}^{n} x_i \cdot y_i}{\left[\sum_{i=1}^{n} x_i^2\right]^{1/2} \left[\sum_{i=1}^{n} y_i^2\right]^{1/2}}$$

where x is the first template, y is the second template, and n is the number of samples in the template. Note that the denominator terms are normalization factors for each template. Thus, three template correlation coefficients are produced: $CC_{BiV\&RV}$, $CC_{BiV\&LV}$, and $CC_{LV\&RV}$. These correlation coefficients between the templates are used to establish bounds to help classify evoked response waveforms. FIG. 8 shows a plot of the template correlation coefficients of the waveforms shown in FIG. 6. As might be expected, the similarity of the BiV and RV waveforms produces a high correlation between the two templates. Alternatively, the lack of similarity between the LV and both the RV and BiV waveform yields a low correlation. Bounds are established at an exemplary ±20 percentage points on either side of the calculated correlation coefficients. These bounds for the template cross-correlations can be used to more specifically detect particular capture events by determining if an evoked response not only highly correlates with one template but also correlates with the other two templates to an expected extent.

Once the templates and bounds have been properly established, the algorithm is ready to determine capture of subsequent paced beats at step E2. Following a pace, a 400 ms portion of the evoked response signal is collected and normalized:

$$ER_{norm} = \frac{ER}{\left[\sum_{i=1}^{n} (ER_i)^2\right]^{1/2}}$$

where ER is the evoked response waveform, and n is the number of samples in the waveform. Next, the ER waveform is cross-correlated with the templates by calculating a correlation coefficient between the normalized evoked response waveform and each normalized template:

$$CC_{ER\&BiV} = \sum_{i=1}^{n} ER_{norm,i} \cdot BiV_{norm,i}$$

$$CC_{ER\&RV} = \sum_{i=1}^{n} ER_{norm,i} \cdot RV_{norm,i}$$

$$CC_{ER\&LV} = \sum_{i=1}^{n} ER_{norm,i} \cdot LV_{norm,i}$$

Next, at steps E3 through E5, the evoked response is classified according to multiple criteria for each of the three possible capture events: BiV, RV, or LV capture. The evoked response may meet the criteria for one or more such events or may not meet any of the criteria. In order to meet the criteria for a particular capture event, the correlation coefficient of the evoked response waveform with the template for that capture event must be above a specified threshold (0.9 in this implementation), and the correlation coefficients of the evoked response waveform with the other must be within the bounds identified at step E1. As an example, assume the ER highly correlates with the BiV template, meeting the first criteria of step E3. If the cross correlations of the ER and the other two templates are within the bounds predicted by the earlier template analysis in step E2, the ER is classified as biventricular capture. In other words, if the ER closely matches the morphology of the BiV template and does not match the other templates in the expected manner, then the waveform is classified as biventricular capture.

After the ER waveform is classified according to the criteria of steps E3 through E5, subsequent steps determine the final detection result. If the ER waveform meets the criteria for both BiV and RV capture, as determined at step E6, then the total energy of the ER waveform in a sub-window 200-300 ms following the pace is utilized as a secondary discrimination criterion at step E7. If the total energy in the subwindow is above or below a specified limit, then RV capture is detected at step E11. Otherwise, BiV capture is detected at step E9. If the ER waveform is classified as meeting the criteria for only one capture event, the algorithm detects either BiV, RV, or LV capture at steps E8 through E13. If the ER waveform is classified as not meeting any other capture event criteria, the algorithm will detect either asystole or a fusion beat. If the total energy in the ER waveform is less than a specified threshold percentage (e.g., 10%) of the energy in the BiV template prior to normalization, as determined at step E14, then asystole is declared at step E15. Otherwise, since the ER waveform has been found to not meet any of the capture event criteria but is still representative of cardiac activity, the pace is classified as a fusion beat at step E16.

f. Selection of the Best Sensing Vector for Morphology-Based Capture Detection

As described above, morphology-based capture detection involves comparing an evoked response waveform during a paced cycle with a template waveform representing capture. That is, an evoked response electrogram is recorded during a paced cardiac cycle, the waveform of the evoked response electrogram is compared with a template waveform representing capture, and capture is determined to have occurred during the paced cardiac cycle if the degree of similarity between the evoked response and template waveforms is a above a specified threshold. The comparison may be performed by a clinician visually inspecting the waveforms or performed by a processor which cross-correlates or otherwise analyzes the waveforms. In either case, distinguishing between a capture and a non-capture situation depends upon there being a morphology difference between the template representing capture and an evoked response electrogram recorded during a cycle in which one or more of the pacing pulses represented by the template fail to achieve capture. The greater is the morphology difference between the two waveforms, the easier it is to distinguish between capture and non-capture. Waveforms with a greater morphology difference when loss of capture occurs or pacing modes are changed inherently yield a greater signal to noise ratio and provide superior accuracy and fusion detection. This morphology difference will generally vary with the sensing vector used to generate the evoked response and template waveforms. A sensing vector refers to the direction in which a wave of depolarization or repolarization gives the highest amplitude electrogram signal and is defined by the spatial arrangement of the sensing electrodes used to generate the electrogram signal. In another aspect of the invention, a morphology-based technique is used to select among a plurality of available sensing vectors to determine the optimum sensing vector for performing morphology-based capture verification performed either by a processor or a clinician visually inspecting displayed evoked response and template waveforms. The technique may be implemented as an automatic system which includes an external programmer in communication with an implanted pacemaker or the pacemaker alone. The technique may also be implemented as a semi-automatic system in which a clinician provides inputs after viewing data generated by the external programmer and/or implanted pacemaker.

A sensing vector for generating the evoked response and template waveforms to be used for morphology-based capture detection may be optimally selected by: 1) comparing electrograms generated by capturing and non-capturing pacing pulses for a plurality of different sensing vectors, and 2) selecting the sensing vector which results in the greatest degree of dissimilarity between the electrograms generated by the capturing and non-capturing pacing pulses. The comparison may be performed by cross-correlating the capturing and non-capturing waveforms. In a biventricular pacing example, where a template representing biventricular capture is cross-correlated with an evoked response waveform in order to verify biventricular capture, an electrogram generated during biventricular capture is cross-correlated with an electrogram generated when biventricular capture is not achieved for the plurality of sensing vectors. The sensing vector for generating the evoked response and template waveforms needed for performing capture detection is then selected as that sensing vector for which the electrograms generated during biventricular capture and no biventricular capture are the least correlated. The electrogram generated when biventricular capture is not achieved for purposes of sensing vector selection may be an electrogram generated during right ventricle-only capture or left ventricular-only capture. In the case where the electrograms are generated by an implantable device, the plurality of sensing vectors is formed by selecting particular switchable electrodes of the device for recording electrograms. In the case where the electrograms are surface ECG's, the plurality of sensing vectors are formed by selecting particular leads of the surface ECG apparatus for recording electrograms. In an exemplary implementation, the sensing vector is selected prior to performing a threshold test for determining an appropriate pacing pulse energy for the pacemaker. The sensing vector could also be selected during a template acquisition routine in which the template representing biventricular capture for comparing to an evoked response is generated.

A specific embodiment of the invention will now be described in the context of biventricular pacing where capture detection, for purposes of pacing threshold determination or implementing an autocapture function, is performed by cross-correlating a BiV evoked response waveform with a template waveform representing BiV capture with a loss of BiV capture detected if the correlation between the two waveforms is below a specified threshold value. (As described above, the BiV evoked response waveform may also be further correlated with templates representing RV-only capture and LV-only capture in order to further classify the evoked response.) In order to select the optimum sensing vector for capture detection, a template representing BiV capture and a template representing LV-only capture and/or RV-only capture are generated for all of the available sensing vectors. The LV-only and RV-only capture templates thus each represent a loss of biventricular capture, and either or both may be used to select the optimum sensing vector. In the former case, one of either the LV-only or RV-only capture templates is compared (e.g., by cross-correlation) with the BiV capture template for each sensing vector, and the sensor vector for which the BiV capture template is most dissimilar to the loss of capture template is selected as the optimum one. In the latter case, the BiV capture template is compared with each of the LV-only and RV-only capture templates for each sensing vector. The optimum sensing vector may then be selected as the one for which the BiV capture template is most dissimilar to both loss of capture templates. For example, cross-correlations between the BiV capture template and each of the LV-only and RV-only templates may be performed for each sensing vector, with the optimum sensing vector selected as the one in which the BiV capture template is least correlated to whichever of the LV-only and RV-only capture templates is most similar to the BiV capture template.

In a modification to the embodiment described above, rather than selecting a single optimum sensing vector for detecting loss of biventricular capture, separate optimum sensing vectors are selected for detecting each type of biventricular capture loss, i.e., loss of RV capture and loss of LV capture. Thus, the optimum sensing vector for determining loss of RV capture is the sensing vector for which the BiV capture template and the LV-only capture template are least correlated, and the optimum sensing vector for determining loss of LV capture is the sensing vector for which the BiV capture template and the RV-only capture template are least correlated. The two optimum sensing vectors may then be used simultaneously in an autocapture system to more sensitively detect a loss of biventricular capture. An algorithm for determining capture thresholds for the RV and LV pacing channels may also employ separate sensing vectors in order to more precisely determine the threshold for each channel. For example, in a capture threshold determination algorithm such as described in FIG. 3A, the capture threshold for the RV channel is found by decreasing the RV pace amplitude during biventricular pacing until loss of biventricular capture is detected by comparing the evoked response with a BiV capture template. This step could be performed using the sensing vector for which the BiV capture template and LV-only capture template are least correlated. Similarly, to find the capture threshold for the LV channel, the LV pace amplitude is decreased during biventricular pacing until loss of capture is detected using the sensing vector for which the BiV capture template and RV-only capture template are least correlated.

Figure 9:
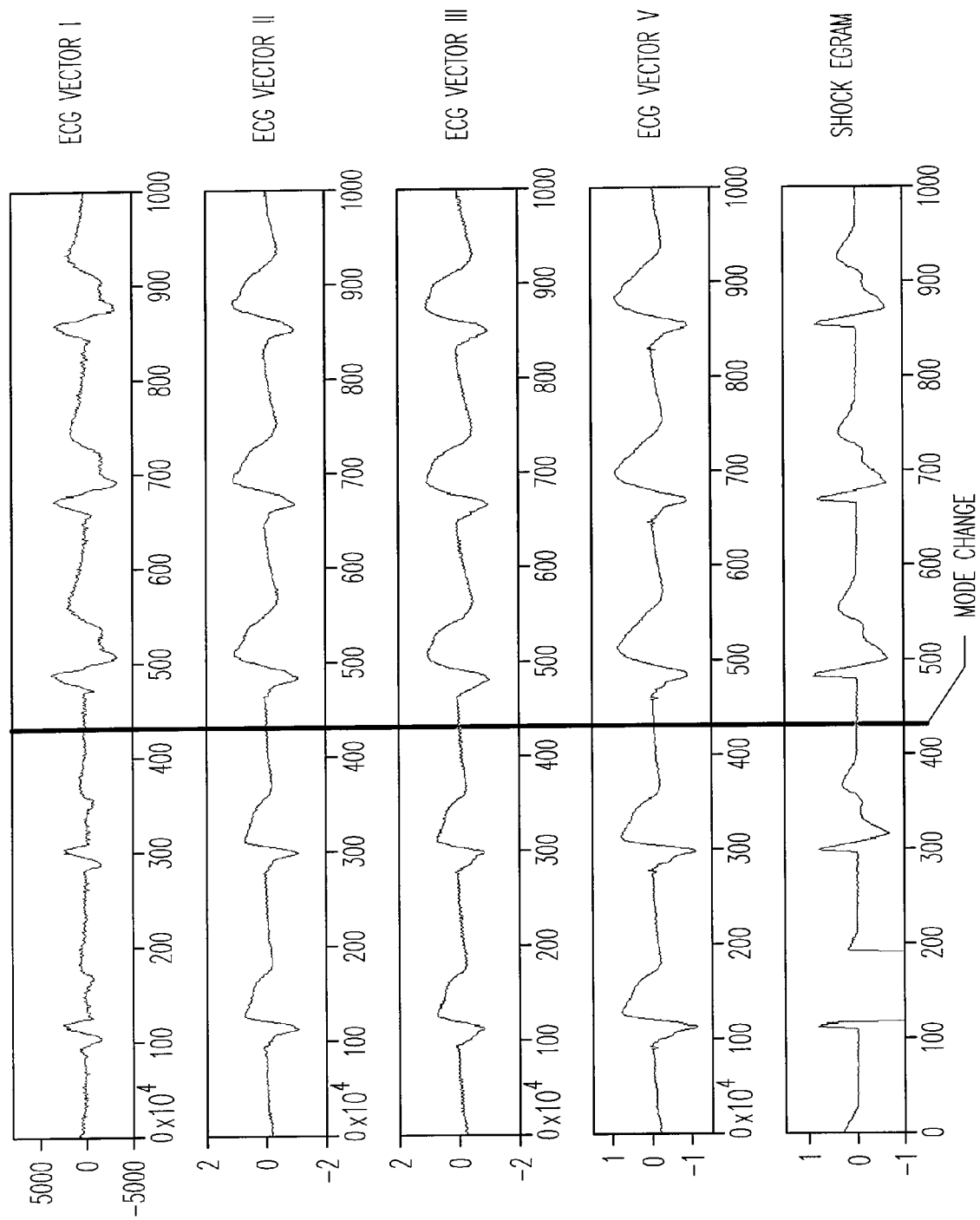
FIG. 9 shows example electrograms from a number of different sensing vectors during a mode switch from BiV to RV pacing.

Multi-site ventricular pacing adds a challenging dimension to cardiac signal analysis during device follow-up. This becomes quite apparent when trying to determine capture mode from ECG or intracardiac electrogram data. A change in pacing mode, for instance from BiV to RV, often creates a significant morphology variation only on certain cardiac vectors. FIG. 9 shows examples of electrograms recorded for a number of different ECG vectors (designated I through V) and a shock channel electrogram during a mode switch from BiV pacing to RV pacing from a particular subject Note that only vector I shows a significant morphology change when the LV lead loses capture. If not viewing vector I, this scenario can be quite confusing or misleading to the clinician. The clinician might not notice a loss of the LV lead and inadvertently not provide heart failure therapy. Alternatively, no change in the cardiac vectors with a commanded change from BiV to RV may cause the clinician to question the capture of the LV lead or the device functionality. A significant morphology change between pacing modes is also critical for the morphology-based techniques of capture verification and threshold determination described above. In FIG. 9, vector I would be the preferred vector to view or analyze when finding the threshold of the left ventricular lead. Other vectors show only slight changes that would most likely be missed by clinicians in real-time and may not be interpreted accurately by a morphology-based capture verification algorithm.

Figure 10:
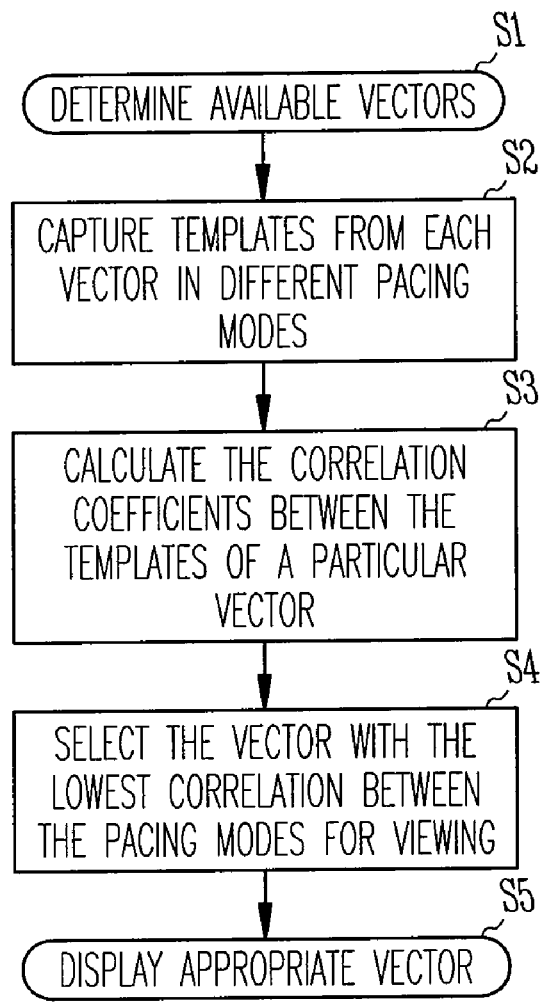
FIG. 10 illustrates an exemplary algorithm for sensing vector selection.

FIG. 10 shows an exemplary algorithm for selecting an optimum sensing vector for morphology analysis which could be performed manually by a clinician operating an external programmer or incorporated as a system into an implantable device and/or external programmer. At step S1, the system determines the available sensing vectors. This information may be pre-programmed into the system or determined from sensor data. For example, if the system is incorporated into a programmer employing an ECG leads-off indicator, the device software could automatically determine the ECG vectors attached to the patient. At step S2, the system collects templates in BiV, RV, and LV modes on all available e-gram and ECG vectors. These templates can be used for capture verification and also represent capturing and non-capturing waveforms for purposes of sensing vector selection. Cross-correlations between the templates are performed at step S3 which indicate the vector with the least similarity in the different modes, and that vector is selected at step S4 as the optimum sensing vector. For instance, in the case of a change from BiV to RV pacing (loss of LV capture), the system would select the vector with the greatest change between BiV and RV modes. Similarly, in the case of a change from BiV to LV pacing (loss of RV capture), the system would select the vector with the greatest change between BiV and LV modes. Finally at step S5, the selected vector or vectors are displayed or otherwise used for morphology analysis.

Figure 11:
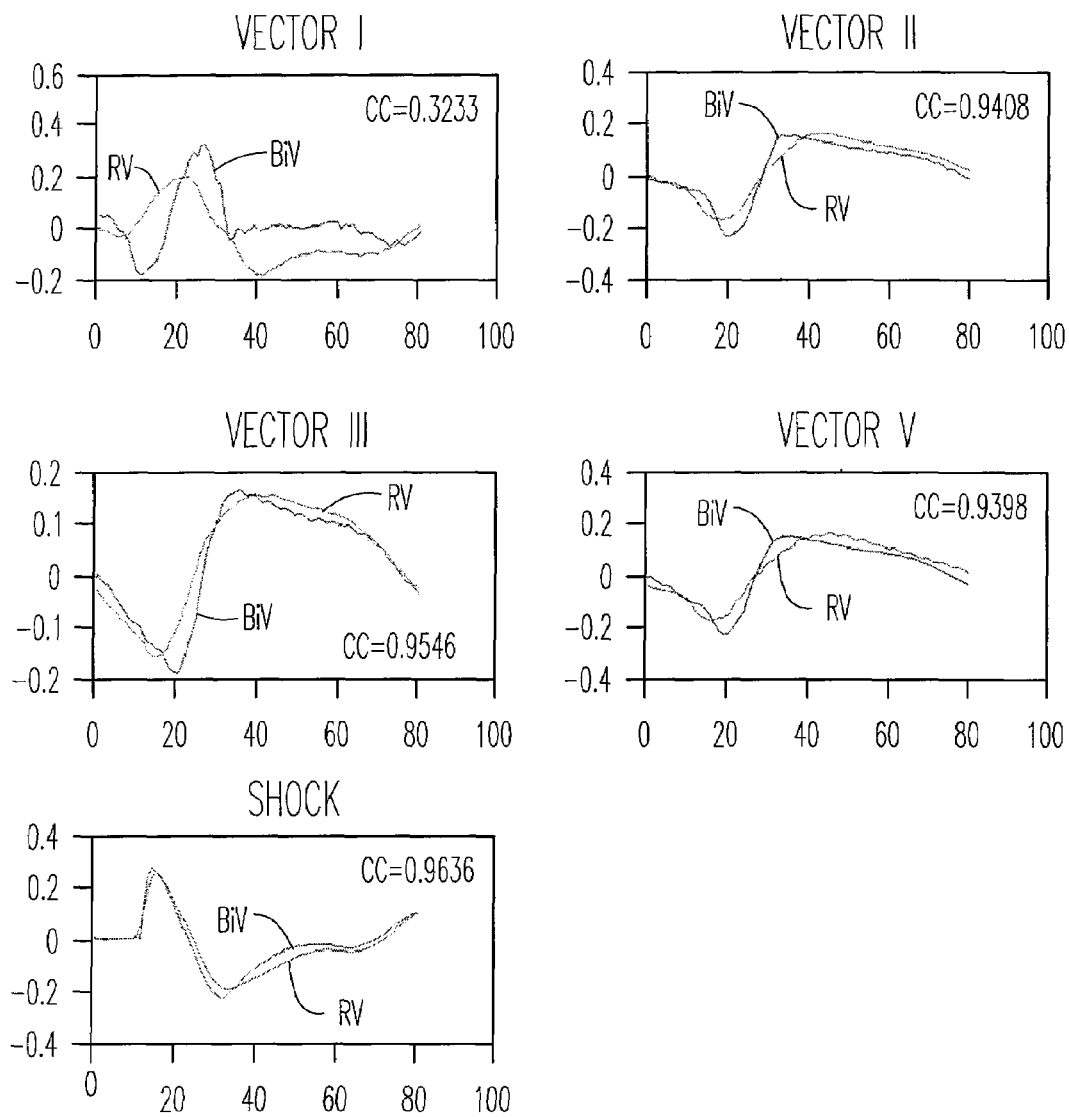
FIG. 11 illustrates the correlations between BiV and RV templates for different sensing vectors.

FIG. 11 illustrates example cross-correlation results of the sensing vector selection analysis just described as performed on the waveforms from FIG. 9. Templates were gathered by averaging evoked responses from each vector in both BiV and RV modes. Following the generation of the templates, the correlation coefficients between the templates of a particular vector in the different modes are calculated to measure the degree of similarity. The correlation coefficients (CC) are calculated as follows:

$$CC = \frac{\sum_{i=1}^{n} x_i \cdot y_i}{\left[\sum_{i=1}^{n} x_i^2\right]^{1/2} \left[\sum_{i=1}^{n} y_i^2\right]^{1/2}}$$

where x is the first template, y is the second template, and n is the number of samples in the template. Note that the denominator terms are normalization factors for each template. The vector with the lowest CC between the two modes indicates the optimal vector for viewing during a capture verification and/or threshold test or for detecting a change in pacing mode. In the case of the data in FIG. 11, vector I clearly displays the lowest correlation, agreeing with the time domain data shown in FIG. 9. Vector I will also provide superior performance if used with a morphology-based capture verification or autothreshold algorithm.

There are many various ways in which the optimum vector selection technique described above could be implemented. For example, an external programmer could automate the change of pacing modes to capture the templates prior to a manual threshold test and automatically display or make a recommendation about the best vector to view. The templates could be captured in the background through the normal programming session so that an extra routine would not be required prior to the threshold tests. The selection of the optimal vector could also be stored in the device for future reference. For instance, if a patient's vector I showed the greatest change because of a change in pacing mode, this vector could automatically be displayed on the screen upon device interrogation. If incorporated with a morphology-based biventricular capture verification and/or autothreshold algorithm as described herein, the optimal vector selection could be performed during the template acquisition routine. The optimal vector would then be used by the capture verification algorithm and could also be displayed on the programmer during an automatic or manual threshold test.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for verifying capture by a cardiac pacemaker, comprising:
   delivering biventricular pacing during a paced cardiac cycle;
   recording an evoked response electrogram during a paced cardiac cycle;
   comparing the waveform of the evoked response electrogram with template waveforms representing biventricular, left ventricle-only, and right ventricle-only capture;
   determining that either biventricular, left ventricle-only, or right ventricle-only capture has occurred during the paced cardiac cycle if the degree of similarity between the evoked response and one of the biventricular, left ventricle-only, or right ventricle-only capture template waveforms is above a specified threshold; and,
   selecting an optimum sensing vector for generating the evoked response and template waveforms by generating biventricular, left ventricle-only, and right ventricle-only capture templates using a plurality of different sensing vectors and selecting the optimum sensing vector as that sensing vector for which the biventricular capture template is least similar to one or both of the left ventricle-only and right ventricle-only capture templates.

2. The method of claim 1 further comprising:
   comparing the waveform of the evoked response electrogram with template waveforms representing biventricular, left ventricle-only, and right ventricle-only capture by cross-correlating the waveform of the evoked response electrogram with the template waveforms representing biventricular, left ventricle-only, and right-ventricle-only capture;
   determining that capture has occurred during the paced cardiac cycle if the correlation between the evoked response and one of the template waveforms is a above a specified threshold.

3. The method of claim 1 further comprising:
   selecting an optimum sensing vector for detecting right ventricle-only capture as that sensing vector for which the biventricular capture template is least similar to the fight ventricle-only template; and,
   selecting an optimum sensing vector for detecting left ventricle-only capture as that sensing vector for which the biventricular capture template is least similar to the left ventricle-only template.

4. The method of claim 1 further comprising selecting the optimum sensing vector as that sensing vector for which the biventricular capture template is least similar to whichever of the left ventricle-only and right ventricle-only capture templates is most similar to the biventricular capture template.

5. The method of claim 1 further comprising selecting the optimum sensing vector as that sensing vector for which the biventricular capture template is least correlated to whichever of the left ventricle-only and right ventricle-only capture templates is most correlated to the biventricular capture template.

6. The method of claim 1 wherein the plurality of sensing vectors are formed by selecting particular switchable electrodes of the pacemaker for recording electrograms.

7. The method of claim 1 wherein the plurality of sensing vectors are formed by selecting particular leads of a surface ECG apparatus for recording electrograms.

8. The method of claim 1 wherein the sensing vector is selected prior to performing a threshold test for determining an appropriate pacing pulse energy for the pacemaker.

9. The method of claim 1 wherein the sensing vector is selected during a template acquisition routine in which a template representing biventricular capture is generated.

10. A system for verifying capture by an implantable cardiac pacemaker, comprising:
    an implantable cardiac pacemaker configured to deliver biventricular pacing;
    an external programmer in communication with the pacemaker via a wireless telemetry link; and,
    wherein the external programmer is configured to:
    store an evoked response electrogram recorded during a paced cardiac cycle;
    compare the waveform of the evoked response electrogram with template waveforms representing biventricular, left ventricle-only, and right ventricle-only capture;
    determine that either biventricular, left ventricle-only, or right ventricle-only capture has occurred during the paced cardiac cycle if the degree of similarity between the evoked response and one of the biventricular, left ventricle-only, or right ventricle-only capture template waveforms is above a specified threshold; and,
    select an optimum sensing vector for generating the evoked response and template waveforms by generating biventricular, left ventricle-only, and right ventricle-only capture templates using a plurality of different sensing vectors and selecting the optimum sensing vector as that sensing vector for which the biventricular capture template is least similar to one or both of the left ventricle-only and right ventricle-only capture templates.

11. The system of claim 10 wherein the external programmer is configured to:
    compare the waveform of the evoked response electrogram with template waveforms representing biventricular, left ventricle-only, and right ventricle-only capture by cross-correlating the waveform of the evoked response electrogram with the template waveforms representing biventricular, left ventricle-only, and right-ventricle-only capture;
    determine that capture has occurred during the paced cardiac cycle if the correlation between the evoked response and one of the template waveforms is a above a specified threshold.

12. The system of claim 10 wherein the external programmer is configured to:
    select an optimum sensing vector for detecting right ventricle-only capture as that sensing vector for which the biventricular capture template is least similar to the right ventricle-only template; and,
    select an optimum sensing vector for detecting left ventricle-only capture as that sensing vector for which the biventricular capture template is least similar to the left ventricle-only template.

13. The system of claim 10 wherein the external programmer is configured to select the optimum sensing vector as that sensing vector for which the biventricular capture template is least similar to whichever of the left ventricle-only and right ventricle-only capture templates is most similar to the biventricular capture template.

14. The system of claim 10 wherein the external programmer is further configured to select the optimum sensing vector as that sensing vector for which the biventricular capture template is least correlated to whichever of the left ventricle-only and right ventricle-only capture templates is most correlated to the biventricular capture template.

15. The system of claim 10 wherein the evoked response electrogram is an electrogram transmitted to the external programmer by the pacemaker and further wherein the plurality of sensing vectors are formed by selecting particular switchable electrodes for incorporating into a sensing channel of the pacemaker for recording electrograms.

16. The system of claim 10 wherein the plurality of sensing vectors are formed by selecting particular leads of a surface ECG apparatus incorporated into the external programmer for recording electrograms.

17. The system of claim 10 wherein the external programmer is configured to automatically select the sensing vector prior to performing a threshold test for determining an appropriate pacing pulse energy for the pacemaker.

18. The system of claim 10 wherein the external programmer is configured to automatically select the sensing vector during a template acquisition routine in which a template representing biventricular capture is generated.

19. An implantable cardiac pacemaker, comprising:
a pacing channel for delivering pacing pulses;
a sensing channel for generating electrogram signals;
a controller for controlling the operation of the pacemaker, wherein the controller is configured to:
store an evoked response electrogram recorded during a paced cardiac cycle;
compare the waveform of the evoked response electrogram with template waveforms representing biventricular, left ventricle-only, and right ventricle-only capture;
determine that either biventricular, left ventricle-only, or right ventricle-only capture has occurred during the paced cardiac cycle if the degree of similarity between the evoked response and one of the biventricular, left ventricle-only, or right ventricle-only capture template waveforms is above a specified threshold; and,
select an optimum sensing vector for generating the evoked response and template waveforms by generating biventricular, left ventricle-only, and right ventricle-only capture templates using a plurality of different sensing vectors and selecting the optimum sensing vector as that sensing vector for which the biventricular capture template is least similar to one or both of the left ventricle-only and right ventricle-only capture templates.

20. The pacemaker of claim 19 wherein the controller is configured to:
compare the waveform of the evoked response electrogram with template waveforms representing biventricular, left ventricle-only, and right ventricle-only capture by cross-correlating the waveform of the evoked response electrogram with the template waveforms representing biventricular, left ventricle-only, and right-ventricle-only capture;
determine that capture has occurred during the paced cardiac cycle if the correlation between the evoked response and one of the template waveforms is a above a specified threshold.

21. The pacemaker of claim 19 wherein the controller is configured to:
select an optimum sensing vector for detecting right ventricle-only capture as that sensing vector for which the biventricular capture template is least similar to the right ventricle-only template; and,
select an optimum sensing vector for detecting left ventricle-only capture as that sensing vector for which the biventricular capture template is least similar to the left ventricle-only template.

22. The pacemaker of claim 19 wherein the controller is configured to select the optimum sensing vector as that sensing vector for which the biventricular capture template is least similar to whichever of the left ventricle-only and right ventricle-only capture templates is most similar to the biventricular capture template.

23. The pacemaker of claim 19 wherein the controller is further configured to select the optimum sensing vector as that sensing vector for which the biventricular capture template is least correlated to whichever of the left ventricle-only and right ventricle-only capture templates is most correlated to the biventricular capture template.

24. The pacemaker of claim 19 wherein the plurality of sensing vectors are formed by selecting particular switchable electrodes for incorporating into a sensing channel of the pacemaker for recording electrograms.

25. The pacemaker of claim 19 wherein the controller is configured to automatically select the sensing vector prior to performing a threshold test for determining an appropriate pacing pulse energy for the pacemaker.

26. The pacemaker of claim 19 wherein the controller is configured to automatically select the sensing vector during a template acquisition routine in which a template representing biventricular capture is generated.

* * * * *

UNITED STATES PATENT AND TRADEMARK OFFICE
CERTIFICATE OF CORRECTION

PATENT NO. : 7,412,287 B2  Page 1 of 1
APPLICATION NO. : 10/744911
DATED : August 12, 2008
INVENTOR(S) : Yonce et al.

It is certified that error appears in the above-identified patent and that said Letters Patent is hereby corrected as shown below:

In column 19, line 37, in Claim 2, before "above" delete "a".

In column 19, line 43, in Claim 3, delete "fight" and insert -- right --, therefor.

In column 20, line 41, in Claim 11, before "above" delete "a".

In column 22, line 7, in Claim 20, before "above" delete "a".

Signed and Sealed this

Twentieth Day of January, 2009

JON W. DUDAS
*Director of the United States Patent and Trademark Office*